United States Patent
Cochran et al.

(10) Patent No.: US 6,967,716 B1
(45) Date of Patent: Nov. 22, 2005

(54) APPARATUS AND METHOD FOR INSPECTING MULTI-LAYER PLASTIC CONTAINERS

(75) Inventors: Don W. Cochran, Novelty, OH (US); Steven D. Cech, Aurora, OH (US)

(73) Assignee: Pressco Technology Inc., Cleveland, OH (US)

( * ) Notice: Subject to any disclaimer, the term of this patent is extended or adjusted under 35 U.S.C. 154(b) by 0 days.

(21) Appl. No.: 10/018,267

(22) PCT Filed: Apr. 21, 2000

(86) PCT No.: PCT/US00/10778

§ 371 (c)(1),
(2), (4) Date: Apr. 15, 2002

(87) PCT Pub. No.: WO00/65327

PCT Pub. Date: Nov. 2, 2000

Related U.S. Application Data

(60) Provisional application No. 60/130,894, filed on Apr. 23, 1999.

(51) Int. Cl.[7] ............................................. G01N 21/00
(52) U.S. Cl. ............................... 356/239.4; 356/240.1; 250/223 B
(58) Field of Search .................... 356/239.1–239.6, 356/240.1; 250/223 B; 209/524, 580, 577, 209/588

(56) References Cited

U.S. PATENT DOCUMENTS

| | | | | |
|---|---|---|---|---|
| 3,778,214 A | * | 12/1973 | Wyeth et al. | ................ 425/526 |
| 4,999,509 A | * | 3/1991 | Wada et al. | ........... 250/559.27 |
| 5,141,110 A | * | 8/1992 | Trischan et al. | ............ 209/524 |
| 5,502,559 A | * | 3/1996 | Powell et al. | .................. 356/73 |
| 5,603,413 A | * | 2/1997 | Mitchum, Jr. | ............... 209/580 |
| 5,794,788 A | * | 8/1998 | Massen | ...................... 209/524 |
| 5,866,917 A | * | 2/1999 | Suzuki et al. | .......... 250/559.27 |
| 5,959,731 A | * | 9/1999 | Jones | .......................... 356/503 |

FOREIGN PATENT DOCUMENTS

JP             402010141 A    *  1/1990

* cited by examiner

Primary Examiner—Hoa Q. Pham
(74) Attorney, Agent, or Firm—Fay, Sharpe, Fagan, Minnich & McKee, LLP

(57) ABSTRACT

This invention relates to an apparatus and method for inspecting multi-layer plastic containers (10). More particularly, the invention relates to such an apparatus and method whereby optical energy absorbing compounds are added to the materials comprising the layer(s) of the container (10) to facilitate inspection thereof. Apparatus comprises a sensor unit (40), an illumination unit (30) for illuminating a portion of electromagnetic spectrum at a near IR wavelength to an inspection zone (20) which is located between the sensor unit (40) and the illumination unit (30). A processing unit (50) which receives an output of the sensor unit (40) and determines the attributes of the multilayer plastic containers (10).

24 Claims, 5 Drawing Sheets

APPARATUS AND METHOD FOR INSPECTING MULTI-LAYER PLASTIC CONTAINERS

This application claims priority to and the benefit of International Application Number PCT/US00/10778 filed Apr. 21, 2000, which claims priority to U.S. Provisional Patent Application No. 60/130,894, filed Apr. 23, 1999.

BACKGROUND OF THE INVENTION

This invention relates to an apparatus and method for inspecting multi-layer plastic containers. More particularly, the invention relates to such an apparatus and method whereby optical energy absorbing compounds are added to the materials comprising the layer(s) of the container to facilitate inspection thereof.

While the invention is particularly directed to the art of inspection, and will be thus described with specific reference thereto, it will be appreciated that the invention may have usefulness in other fields and applications.

The application of standard machine vision techniques to inspect the structural integrity of formed plastic food and beverage containers is well established practice. These innovations have proven to be very useful quality and process control tools which allow the manufacturers of these products to improve both the productivity and quality resultant from their manufacturing processes.

A recent trend in the area of plastic container manufacturing is the migration to multi-layer container construction. As part of this trend, plastic container manufacturers have evolved their process to the point wherein the container structures which they manufacture are comprised of multiple layers of unique polymer compounds, each specially formulated to perform a different container-related function. For example, in new multi-layer containers, one layer of the product might be specially designed to prevent the transport of oxygen through the container walls while another layer might provide the container with structural integrity. While the different layers may have unique chemical formulations and provide unique performance attributes to the container, the various components of a multi-layer plastic container will most likely have very similar optical properties, at least within the visible range of the electromagnetic spectrum. More specifically, the index of refraction and optical transmission of these different materials are generally quite similar. This optical similarity is not accidental. In order to maintain the look consumers have become accustomed to with regard to plastic food and beverage containers, the manufacturers have, during the formulation of suitable multi-layer components, been careful to maintain constant the optical properties of the polymers. This fact is significant in relationship to the process of automated inspection of plastic containers. Many prior art machine vision systems utilize CCD cameras sensitive to radiation in the visible wavelength range and a suitable visible light source operated as a backlight. In this fashion, the structural integrity of the container is checked for manufacturing flaws. Because the various layers of a multi-layer plastic container all have very similar optical properties in the visible wavelength range, the selective inspection of the individual layers of a multi-layer container would be extremely hard to do using state-of-the-art machine vision solutions. While it would be possible to detect a defect extending through the container wall, the ability to detect the presence or absence of a layer type, in part or in whole, would be next to impossible. The similar optical properties of the corresponding layers and the lack of image contrast which directly results makes layer-specific inspection impossible using state-of-the-art technology.

The method and apparatus to be disclosed herein overcomes the limitations of state-of-the-art inspection systems describing a method and associated hardware which would allow robust inspection of multi-layer plastic containers. Further, the present invention is a unique method of employing machine vision techniques which incorporate cameras as the sensors and process the resultant image to determine, in a very robust way, the status of the various layer(s) in a plastic bottle.

SUMMARY OF THE INVENTION

The invention relates to an apparatus and method whereby optical energy absorbing compounds are added to materials comprising the layers of the container to facilitate inspection thereof.

In one aspect of the invention, a machine vision apparatus comprises a sensor device comprising an array of photosensitive elements operative to be sensitive to radiation within the near IR portion of the electromagnetic spectrum, a source of electromagnetic radiation wherein a portion of an emitted spectrum thereof is within the near IR portion of the electromagnetic spectrum, part detection, tracking, and conveyance means operative to interact with multi-layer containers under test and maneuver the containers into an advantageous position between the sensor device and source and to provide instrument control signals to both the sensor device and source wherein the containers have selectively absorptive dyes, a processing means which receives the output of the sensor device and executes processing operations to analyze attributes based on a presence of selectively absorptive dyes acting in the near IR portion of the electromagnetic spectrum, and a means which receives the processed output of the processing means and acts to facilitate one of rejecting and marking for subsequent action the container based on the attributes analyzed.

In another aspect of the invention, a method comprises steps of forming a container having a plurality of polymer layers—each polymer layer being formulated to perform a different set of container-related functions, selectively adding optical absorbing compounds acting in the near IR wavelength range to the plurality of polymer layers, disposing the container between the sensing means and the source of near IR electromagnetic radiation, irradiating the source to generate near IR electromagnetic radiation, sensing the near IR electromagnetic radiation by the sensing means, and determining the attributes of the container based on the sensing.

Further scope of the applicability of the present invention will become apparent from the detailed description provided below. It should be understood, however, that the detailed description and specific examples, while indicating preferred embodiments of the invention, are given by way of illustration only, since various changes and modifications within the spirit and scope of the invention will become apparent to those skilled in the art.

DETAILED DESCRIPTION OF THE PREFERRED EMBODIMENTS

Figure 1:
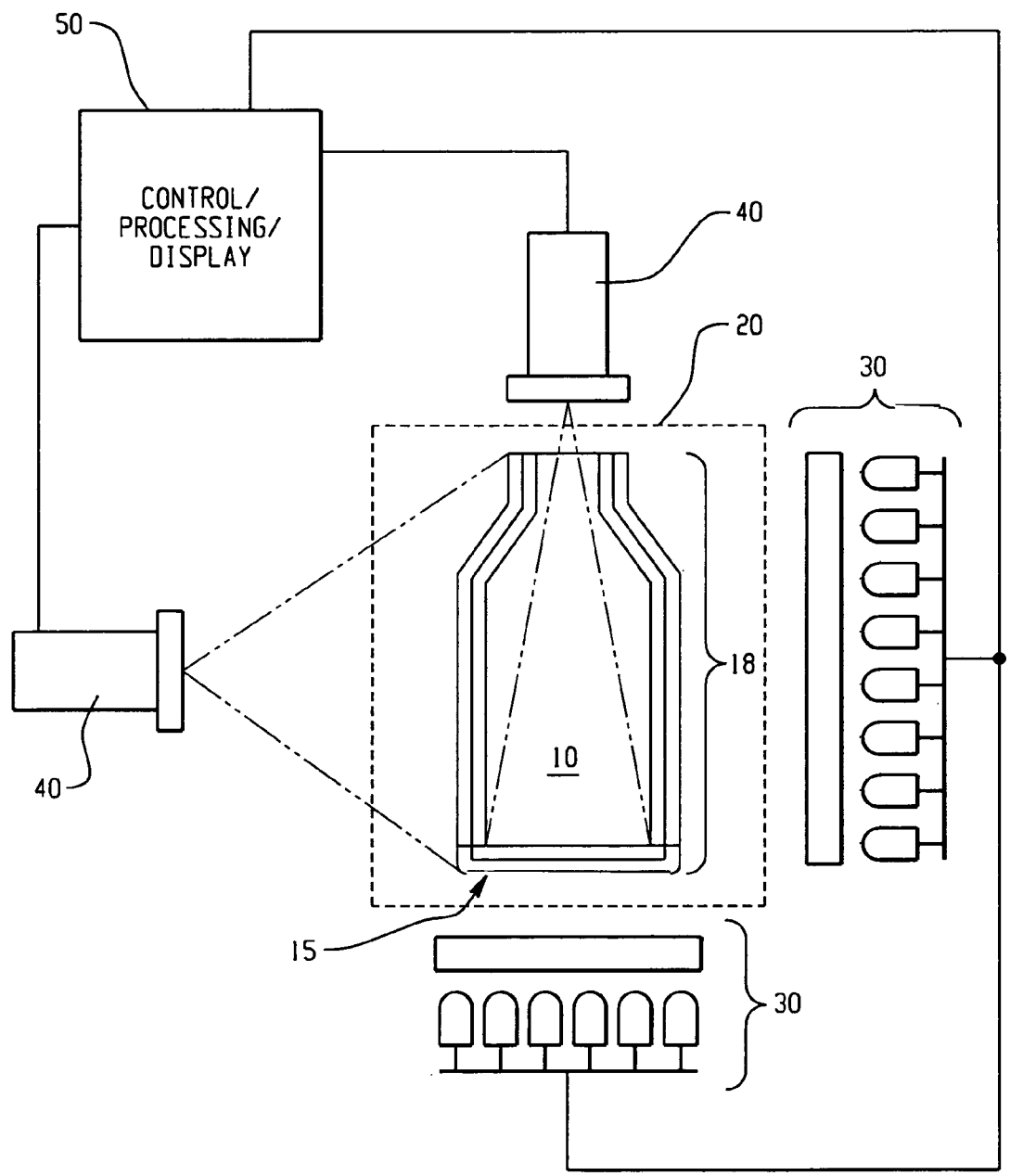
FIG. 1 is a schematic representation of a preferred embodiment of the present invention.

The disclosed method and invention is directed to adding unique amounts and/or types of optical energy absorbing compounds to the formulated polymers comprising the layer(s) of material forming, for example, plastic containers at the time of their preparation. These absorbing materials preferably possess the attribute of selectively absorbing, in a well-controlled fashion, an amount of near infrared (near IR) light passing through its volume. The near IR wavelength range which is referenced here extends from approximately 700 nm to 1000 nm. The theorized absorbing materials or infrared dyes are preferably added to the various layer chemistries for the sole purpose of enabling a thorough inspection of the container which will eventually be formed from them. The infrared dyes which are preferably deployed would typically be highly transmissive in the 400 nm to 700 nm visible wavelength range. In this fashion, their presence within the various plastic layers is preferably unnoticed by human observers. However, a sensor or a CCD camera, which typically has a spectral response extending from the visible range out to about 1000 nm in the near IR range, properly disposed and working in combination with a source of near IR illumination, could be used to inspect the various layers of a multi-layer plastic container.

The use of markers (e.g. the use of substances for the sole purpose of enabling the manual and/or automated inspection of and object) is not a novel concept. In this regard, the use of UV fluorescent dyes to aid in the automatic inspection of products is known. Also, the concept of formulating and applying IR dyes and inks to mark products is an established practice. The use of IR inks in bar coding applications is also known. These are generally in the category of "invisible inks" applied upon the surface of a product for the purpose of reading or tracking.

However, the application of IR dyes within the various layers of a plastic container to aid in the subsequent inspection of the formed container is a novel improvement to the existing state-of-the-art of machine vision technology. The prior art UV marker innovations referenced above have proven to be of limited value in high speed automated inspections due to a lack of adequate UV-induced signal strength. The amount of UV light energy which is available from all reasonably applied commercial sources is limited to start. The situation is made worse by the fact that a lossy conversion factor (UV radiation input energy to visible light output energy) further reduces the light available for detection by a camera. In high speed applications where short camera exposure times are required to properly stop the action of the moving parts, the amount of UV-induced light is insufficient for proper inspection. This is because the UV as typically used currently is a down conversion method whereby the coating or ink or additive is such that when exposed to ultra-violet light it fluoresces with the production of light in the visible light spectrum (i.e. between 400 nm and 700 nm). This so-called "down conversion" is very inefficient and results in an inadequate amount of light being produced to facilitate high quality high speed inspection as explained above.

But, by using a UV light source which is deployed to project through the part being inspected, then a UV light blocking additive would serve to reveal areas that do not have the layer which contains such market additive. This assumes, of course, that a sensor or camera is being used that is directly sensitive to the UV light frequency being used. It can be appreciated, however, by one skilled in the art that UV blocking markers could be used instead of or in addition to the IR blocking markers where desirable. For example, a UV blocking "marker" may already be present because it may have been added to preserve freshness of the food, etc. but it could, with this invention, serve double duty.

An IR marker approach is preferred over a similar UV marker approach because the available signal intensity achievable using commercially available IR sources of energy is orders of magnitude higher than what can be achieved in the UV wavelength range. In addition, the IR marker technique relies upon the direct detection of IR radiation. The CCD cameras are typically highly responsive to near IR energy and, thus, a lossy conversion efficiency to the visible range is avoided.

The addition of an IR dye to the polymer chemistry of a container layer is a fundamentally different process as compared to the process of printing an IR symbol to the surface of manufactured part. In the former, the dye becomes an integral part of the raw material, perhaps added by the polymer manufacturer, at the earliest stages of the manufacturing process or could be introduced by way of colorant or other process chemical additive. In this manner, the marker is available to be used to enhance inspection at the earliest stages, or in any stage, of the container manufacturing process. This would mean that the inspection could be performed at the preform stage during mold qualification, or on-line as they are exiting the molding machine or after the bottles are blown. This is quite different from the application of a printed IR label which is typically applied at the end of the manufacturing process and serves no useful function with regard to product quality inspection, instead being limited to inventory control and tracking functions.

FIG. 1 is a schematic representation of the preferred embodiment of the subject invention. A multi-layer plastic container 10 composed of plastic layers suitably dyed with IR absorbing dyes is allowed to pass through an inspection zone 20. Although different configurations of sensors or cameras could be implemented depending upon the inspection needs and application specification, in the preferred embodiment, two or more camera/lens assemblies 40 are positioned to acquire images of the container 10. One camera/lens assembly 40 would typically be positioned to acquire an image of the base of the container 15 while two or more camera/lens assemblies 40 would typically be deployed to acquire image(s) of the top/neck/sidewall portion of the container. Positioned opposite to each camera/lens assembly 40 will be an appropriate IR light source 30. The preferred embodiment of the IR light sources 30 will be an array of IR emitting solid-state light emitting diodes (LEDs). The camera/lens assemblies 40 and IR light sources 30 are connected to a Control/Processing/Display Module 50 which will be used to facilitate either manual or automatic inspection of the plastic container 10 for pre-defined defects.

Figure 2:
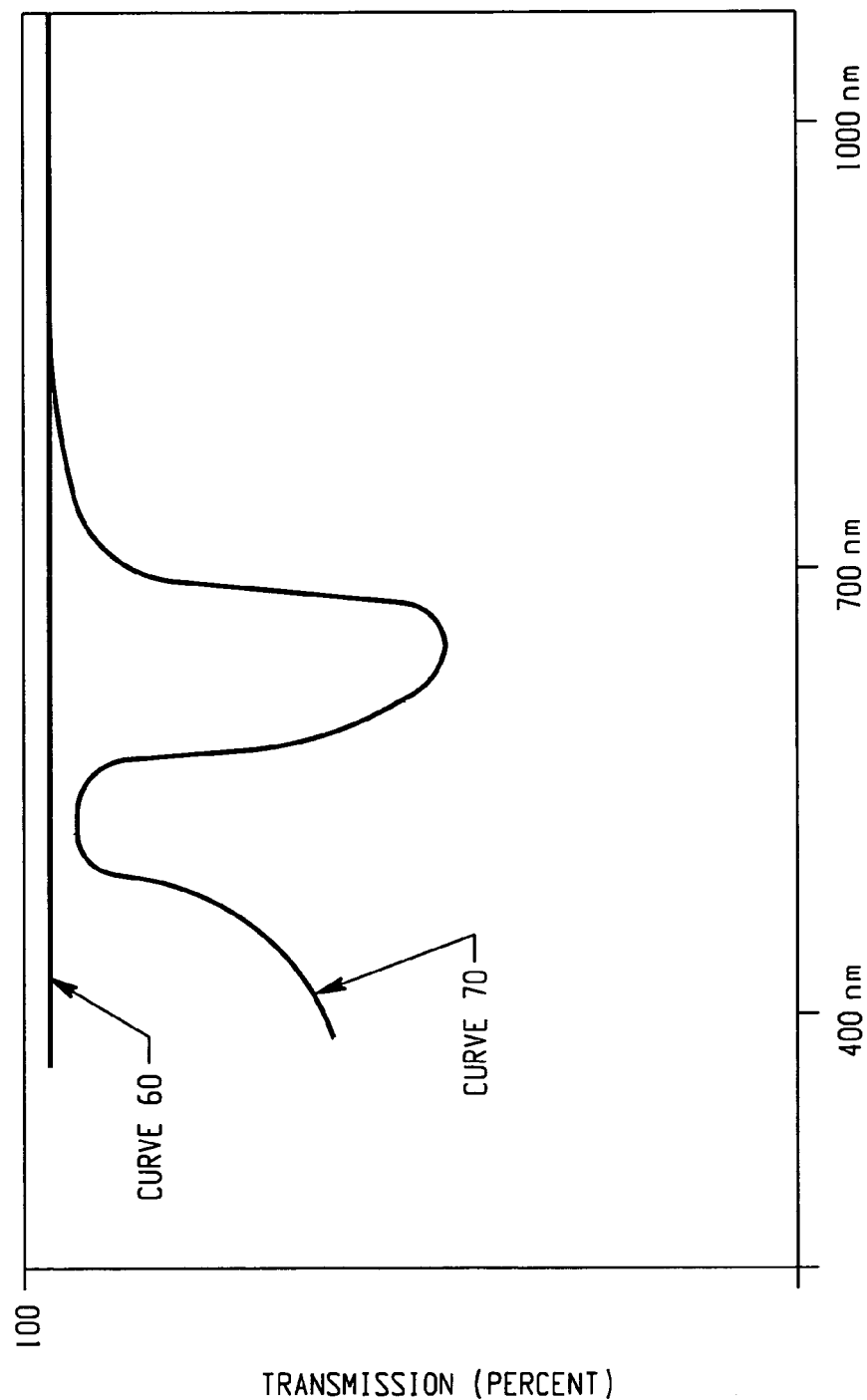
FIG. 2 is a graph showing spectral transmission curves for two materials typically used in the construction of plastic containers.
Figure 3:
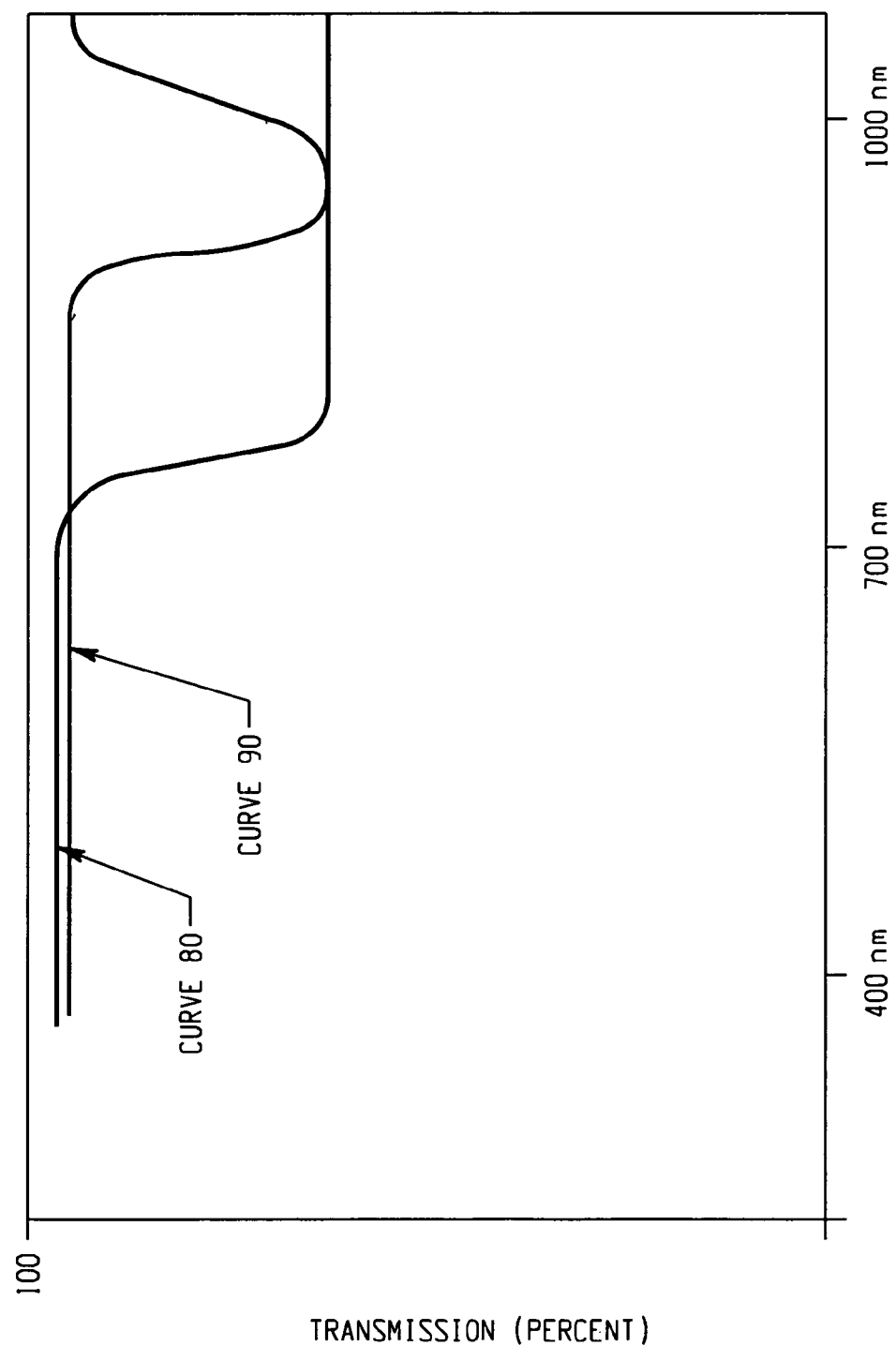
FIG. 3 is a graph showing spectral transmission curves for two materials that have been dyed with infrared material.

Limiting the discussion temporarily to a two layer container for the sole purpose of further clarifying the subject invention, the spectral transmission curves described in FIGS. 2 and 3 are now referenced. FIG. 2 depicts the spectral transmission curves for two plastics typically used in the construction of plastic containers. Curve 60 depicts a plastic which would be described as a clear plastic. The optical transmission of the plastic is very high (near 100%) throughout the important 400 nm to 700 nm visible wavelength range. A high, uniform optical transmission are the measurable attributes of an object defined as clear. Curve 70 shows the same plastic after a green dye has been added to the formula.

This curve depicts a material which has a reduced transmission at the lower wavelengths (blue region) of the visible spectrum. The optical transmission increases to a peak near 100% at 550 nm (green region) and then dramatically falls off within the longer wavelength regions of the visible spectrum (red range). Outside the visible range, the transmission of the plastic quickly rises to the level of the clear plastic curve 60 and remains that way throughout the rest of the 700 nm to 1000 nm near IR region. This behavior, selective absorption in the visible range/no effect in the IR range, is typical of dyes which act within the visible spectrum.

FIG. 3 illustrates two spectral transmission curves of suitable IR dyed plastics as disclosed by this invention. Curve 80 represents the transmission of one type of plastic which would appear to clear to a human observer because of its high transmission in the 400 nm to 700 nm visible wavelength range. This plastic has, however, a well-defined spectral absorption starting at approximately 750 nrm. Curve 90 has a similar IR absorption which takes effect at approximately 850 nm. With both of these plastics contained in adjacent layers within the container structure, the plastics would be visibly indistinguishable but capable of being robustly detected and inspected using the hardware implementation defined by this invention.

Anyone expert in the field of machine vision, i.e. one of ordinary skill in this art, would be able to define several inspection setups which would allow the two plastic types defined by Curves 80 and 90 to be thoroughly inspected while simultaneously present with the field of view of the camera/lens assemblies 40. The spirit of the disclosed invention covers all reasonable combinations of plastic materials and IR or UV absorbing or blocking dyes which can be conceived of and potentially deployed. Potentially, many different layers could be effectively detected and evaluated for quality with the right combination of markers added for absorption at different frequencies or different blocking percentages. In this regard, for example, the existence, thickness and/or integrity (e.g. presence or absence of pinholes) of the layer(s) could be analyzed. Moreover, the invention could also be applied to containers having only a single layer. In this case, the overall quality, thickness and\or integrity of the layer would likely be the primary focus of inspection. Further, the invention would also have usefulness in the inspection of other types of items beyond containers such as plastic sheet material of a single or multiple layer configuration.

Figure 4:
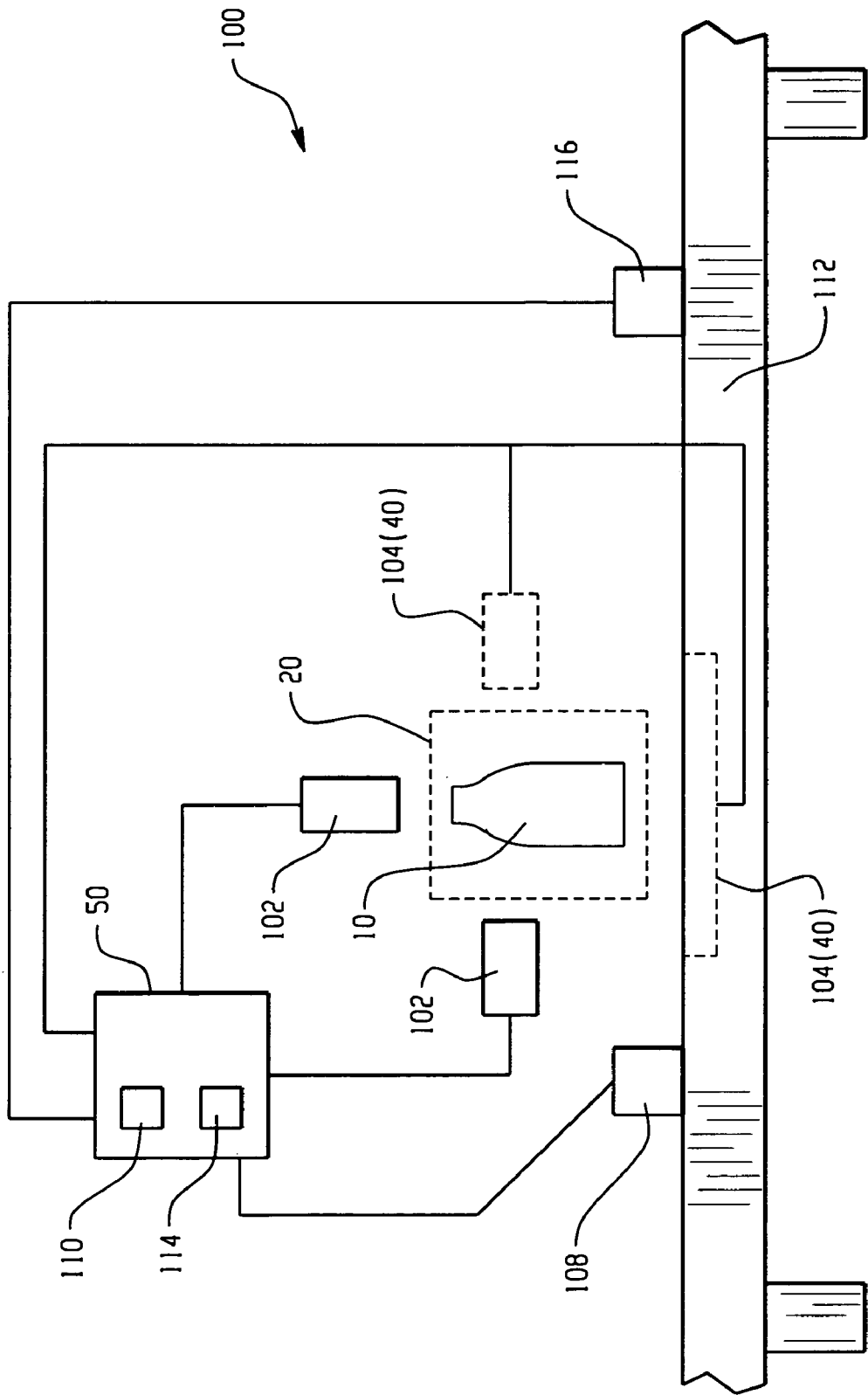
FIG. 4 shows an implementation of the invention.

It should be apparent upon a reading of the detailed description hereof, that the invention of the present application can be implemented in a machine vision apparatus and/or system. Referring more specifically to FIG. 4, a system 100 incorporating the invention of FIG. 1 comprises a sensor device(s) 102 and a source(s) of electromagnetic radiation 104. The sensor device is preferably an array of photosensitive elements which, as an example, may take the form of a charge-coupled device (CCD) based camera(s). The source is preferably a source of electromagnetic radiation wherein a significant portion of the emitted spectrum thereof is within the near infrared (IR) portion of the electromagnetic spectrum. Preferably, the source is an array of light-emitting diodes (LEDs). Also shown in FIG. 4 is a part detector 108, tracking system 110 and conveyance means 112 which are all operative to interact with the multilayer containers 10 under test and are used to both maneuver the containers into an advantageous position between the sensor and source, as well as to provide instrument control signals to both the sensor and the source. Of course, the multilayer containers under test preferably have selectively absorptive dyes which facilitate inspection under the invention. Also shown in FIG. 4 is a processing means 114 which receives the output of the sensor device and executes processing operations which are specifically tuned to analysis attributes which result from the presence of the selectively absorbtive dyes acting in the near infrared portion of the electromagnetic spectrum. Also included in the system 100 is a reject/mark device 116 which receives the process output of the processing means and acts to physically reject, or otherwise mark for subsequent action, the containers or objects determined to be out of or, alternatively, within the specification as previously standardized and encoded within the processing means. It should further be appreciated that the LED emitters of the preferred embodiment may be selectively pulsed to facilitate stopping the action of rapidly moving multilayer containers under test.

Figure 5:
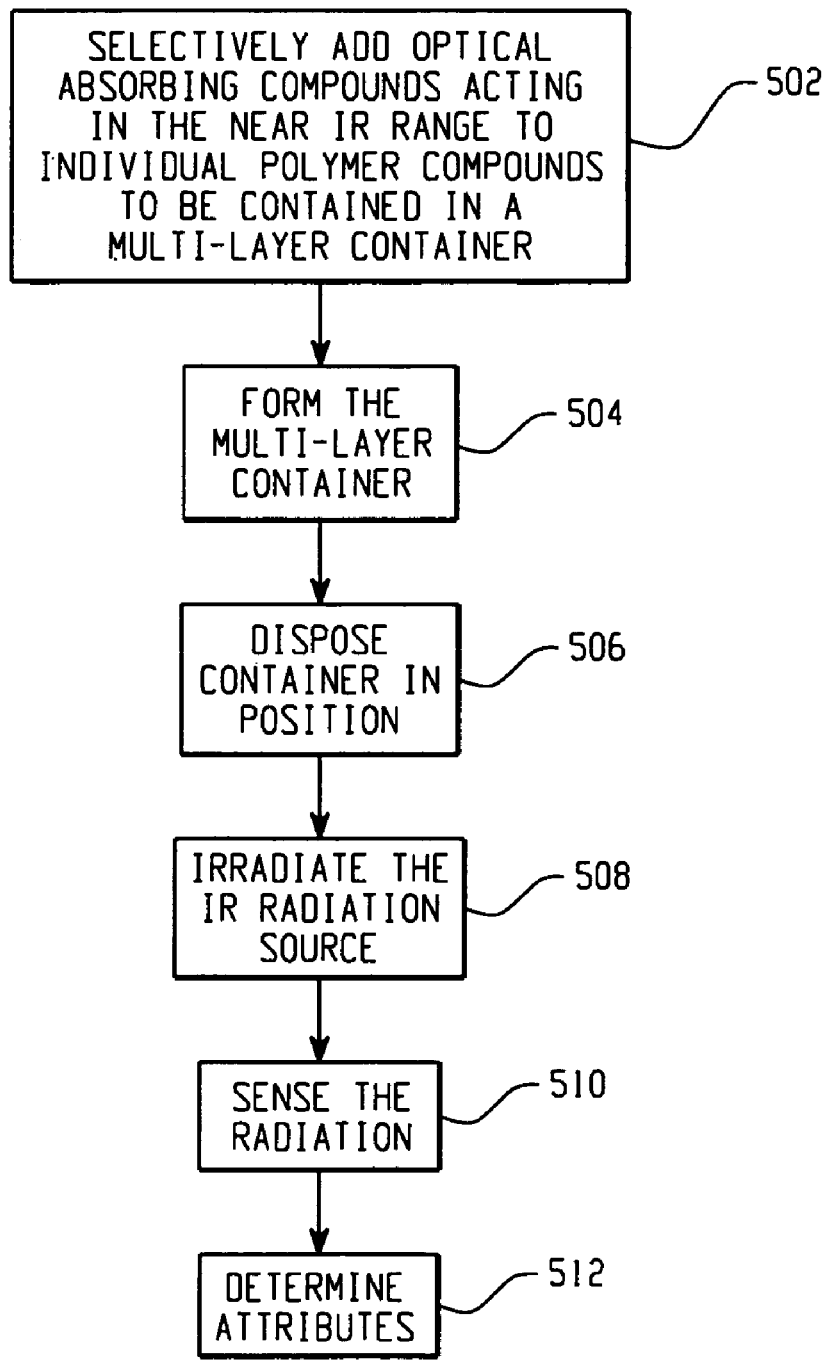
FIG. 5 is a flowchart according to the present invention.

In operation, it is to be appreciated that the method of the present invention useful in this system of FIG. 4 includes, with reference to FIG. 5, prior to the formation process, selectively adding optical absorbing compounds to the polymer layers (step 502). Preferably, the optical absorbing compounds act in the near IR wavelength range. Next, a container having the plurality of polymer layers (e.g. two or more unique polymer layers) is formed whereby each polymer layer is specifically formulated to perform a different set of container related functions (step 504). For inspection purposes, the container is then disposed between a sensing means and a source of near IR electromagnetic radiation (step 506). Preferably, this disposing comprises maneuvering the container into an advantageous position between the sensing means and the source means. The source is then activated or irradiated with near IR electromagnetic radiation (step 508). Next, the radiation is sensed by the sensor device(s), or means (step 510). The attributes of the container (e.g. structural integrity) are then determined based on the sensing (step 512). It should be appreciated that the method may further comprise rejecting or otherwise marking for subsequent action the container or object determined to be out of or alternatively, within specifications as previously standardized and encoded within the processing means of the system. This rejection or marking could be based on a determination of the state, quality or acceptability of the container (which may be based on the determination of attributes).

The above description merely provides a disclosure of particular embodiments of the invention and is not intended for the purpose of limiting the same thereto. As such, the invention is not limited to only the above described embodiments. Rather, it is recognized that one skilled in the art could conceive alternative embodiments that fall within the scope of the invention. The spirit of the disclosed invention should in no way be limited by the very narrow and simplified case outlined as the preferred embodiment.

Having just described the invention, we claim:

1. A method for inspecting attributes of containers useful in a system having at least one sensing means and a source of non-visible electromagnetic radiation, the method comprising steps of:

selectively adding optical absorbing compounds acting in the non-visible wavelength range to a plurality of polymer layers;

forming a container having the plurality of polymer layers, each polymer layer being formulated to perform a different set of container-related functions;

disposing the container between the sensing means and the source of non-visible electromagnetic radiation;

utilizing the source to generate non-visible electromagnetic radiation;

sensing the non-visible electromagnetic radiation by the sensing means; and, determining the attributes of individual layers of the container based on the sensing by analyzing the individual layers of the container based on a presence of the selectively added optical absorbing compounds acting in the non-visible wavelength range.

2. The method of claim 1 further comprising determining a state, quality, or acceptability of the container based on sensing and determining.

3. The method of claim 2 further comprising one of rejecting and marking for subsequent action the container based on the state, quality or acceptability of the container.

4. The method as set forth in claim 1 wherein the forming comprises forming the container with at least a first layer and a second layer.

5. The method as set forth in claim 4 wherein the first layer has a first spectral absorption range and the second layer has a second spectral absorption range.

6. The method as set forth in claim 1 wherein the determining comprises determining the attributes for each layer simultaneously.

7. The method as set forth in claim 1 wherein the attributes comprise at least one of existence, thickness, and integrity.

8. The method as set forth in claim 1 wherein the non-visible electromagnetic radiation is near IR radiation and the non-visible wavelength range is near IR wavelength range.

9. A machine vision apparatus comprising:

a sensor device comprising an array of photosensitive elements operative to be sensitive to radiation within the non-visible portion of the electromagnetic spectrum;

a source of electromagnetic radiation wherein a portion of an emitted spectrum thereof is within the non-visible portion of the electromagnetic spectrum;

part detection, tracking, and conveyance means operative to interact with multi-layer containers under test and maneuver the containers into an advantageous position between the sensor device and source and to provide instrument control signals to both the sensor device and source;

a processing means which receives output of the sensor device and executes processing operations to analyze attributes of individual layers of the container based on a presence of selectively absorptive dyes compounds, within selected layers, acting in the non-visible portion of the electromagnetic spectrum; and, a means which receives the processed output of the processing means and acts to facilitate one of rejecting and marking for subsequent action the container based on the attributes analyzed.

10. The apparatus of claim 9 wherein the source comprises an array of solid state emitters.

11. The apparatus of claim 10 wherein the solid state emitters are pulsed.

12. The apparatus as set forth in claim 9 wherein the containers under test include at least a first layer and a second layer.

13. The apparatus as set forth in claim 12 wherein the first layer has a first spectral absorption range and the second layer has a second spectral absorption range.

14. The apparatus as set forth in claim 9 wherein the processing means is operative to receive the output of the sensor device and execute the processing operations for layers simultaneously.

15. The apparatus as set forth in claim 9 wherein the attributes comprise at least one of existence, thickness and integrity.

16. The apparatus as set forth in claim 9 wherein the non-visible portion of the electromagnetic portion is the near IR portion of the electromagnetic spectrum.

17. A system for inspecting attributes of an item, the item having a plurality of polymer layers, individual polymer layers being formulated to perform a different set of functions and at least one layer including an optical absorbing compound acting in the non-visible wavelength range, the system comprising:

means for generating non-visible electromagnetic radiation;

means for sensing the non-visible electromagnetic radiation;

means for disposing the item between the sensing means and the generating means; and, means for determining attributes of individual layers of the item.

18. The system as set forth in claim 17 further comprising a means for determining a state, quality or acceptability of the container based on output from the means for sensing and the means for determining.

19. The system as set forth in claim 18 further comprising means for rejecting and marking for subsequent action the item based on the state, quality or acceptability of the container.

20. The system as set forth in claim 17 wherein the means for determining comprises means for determining the attributes for each layer simultaneously.

21. The system as set forth in claim 17 wherein the attributes comprise at least one of existence, thickness, and integrity.

22. The system as set forth in claim 17 wherein the item comprises at least a first layer having a first spectral absorption range and a second layer having a second spectral absorption range.

23. The system as set forth in claim 17 wherein the non-visible wavelength range is the near IR wavelength range and the non-visible electromagnetic radiation is near IR electromagnetic radiation.

24. A method for inspecting attributes of an item useful in a system having at least one sensing means and a source of non-visible electromagnetic radiation, the method comprising steps of:

forming the item having a plurality of layers, wherein at least one individual layer has a unique spectral absorption curve relative to other layers;

disposing the item between the sensing means and the source of non-visible electromagnetic radiation;

utilizing the source to generate non-visible electromagnetic radiation;

sensing the non-visible electromagnetic radiation by the sensing means; and, determining the attributes of individual layers of the item based on the sensing by analyzing the at least one individual layer having the unique spectral absorption curve relative to the other layers.

* * * * *